(12) United States Patent
Luo et al.

(10) Patent No.: US 9,364,493 B2
(45) Date of Patent: Jun. 14, 2016

(54) METHODS AND COMPOSITIONS FOR ENHANCING THE UPTAKE OF THERAPEUTIC AGENTS BY TARGET CELLS

(75) Inventors: Yongzhang Luo, Beijing (CN); Yang Chen, Beijing (CN); Yan Fu, Beijing (CN); Lin Jia, Beijing (CN); Guodong Chang, Beijing (CN)

(73) Assignees: Tsinghua University, Beijing (CN); Beijing Protgen LTD., Beijing (CN)

( * ) Notice: Subject to any disclaimer, the term of this patent is extended or adjusted under 35 U.S.C. 154(b) by 0 days.

(21) Appl. No.: 14/008,428

(22) PCT Filed: Mar. 28, 2012

(86) PCT No.: PCT/CN2012/073202
§ 371 (c)(1),
(2), (4) Date: Dec. 4, 2013

(87) PCT Pub. No.: WO2012/130141
PCT Pub. Date: Oct. 4, 2012

(65) Prior Publication Data
US 2014/0147492 A1 May 29, 2014
US 2014/0335152 A2 Nov. 13, 2014

(30) Foreign Application Priority Data
Mar. 28, 2011 (CN) .......................... 2011 1 0085338

(51) Int. Cl.
| | | |
|---|---|---|
| A61K 38/00 | (2006.01) |
| A61K 31/7048 | (2006.01) |
| A61K 38/39 | (2006.01) |
| A61K 39/395 | (2006.01) |
| A61K 9/00 | (2006.01) |
| A61K 9/127 | (2006.01) |
| A61K 47/48 | (2006.01) |
| A61K 31/065 | (2006.01) |
| A61K 31/718 | (2006.01) |
| A61K 45/06 | (2006.01) |
| A61K 31/365 | (2006.01) |
| A61K 31/724 | (2006.01) |
| A61K 38/17 | (2006.01) |

(52) U.S. Cl.
CPC ........... *A61K 31/7048* (2013.01); *A61K 9/0019* (2013.01); *A61K 9/127* (2013.01); *A61K 31/065* (2013.01); *A61K 31/365* (2013.01); *A61K 31/718* (2013.01); *A61K 31/724* (2013.01); *A61K 38/1709* (2013.01); *A61K 38/39* (2013.01); *A61K 39/395* (2013.01); *A61K 45/06* (2013.01); *A61K 47/48215* (2013.01)

(58) Field of Classification Search
None
See application file for complete search history.

(56) References Cited

U.S. PATENT DOCUMENTS

| | | | | |
|---|---|---|---|---|
| 4,812,312 A | * | 3/1989 | Lopez-Berestein et al. | .. 424/417 |
| 2006/0134605 A1 | * | 6/2006 | Folkman et al. | ................. 435/4 |
| 2010/0285103 A1 | * | 11/2010 | Luo et al. | ..................... 424/450 |
| 2012/0157380 A1 | * | 6/2012 | Wang et al. | ..................... 514/7.4 |
| 2015/0030701 A1 | * | 1/2015 | Breaker et al. | ................ 424/663 |

OTHER PUBLICATIONS

Migalovich et al Cancer Research vol. 69 p. 5610 (2009).*
Migalovich, H.S. et al., "Harnessing Competing Endocytic Pathways for Overcoming the Tumor-Blood Barrier: Magnetic Resonance Imaging and Near-Infrared Imaging of Bifunctional Contrast Media," Cancer Research, 2009, vol. 69, No. 13, pp. 5610-5617.

* cited by examiner

*Primary Examiner* — Sheela J Huff
(74) *Attorney, Agent, or Firm* — Rothwell, Figg, Ernst & Manbeck P.C.

(57) ABSTRACT

The present invention relates to a new use of a known medicament. Specifically, the invention relates to methods and compositions for enhancing the therapeutic efficacy of a therapeutic agent by increasing the uptake of the therapeutic agent by target cells, and in particular relates to a pharmaceutical composition comprising a regulating agent of lipid raft/caveolae-dependent endocytic pathway and some therapeutic agents, such as anti-tumor agents. The invention also relates to a method for screening a regulating agent of lipid raft/caveolae-dependent endocytic pathway capable of enhancing the therapeutic efficacy of anti-tumor agents.

14 Claims, 5 Drawing Sheets

METHODS AND COMPOSITIONS FOR ENHANCING THE UPTAKE OF THERAPEUTIC AGENTS BY TARGET CELLS

CROSS-REFERENCE OF THE RELATED APPLICATION

The present application is a 35 U.S.C. §371 National Phase Entry Application of PCT/CN2012/073202, filed 28 Mar. 2012, designating the United States, which in turn claims priority to Chinese Patent Application No. 201110085338.8, filed on 28 Mar. 2011, both of which are incorporated herein by reference.

FIELD OF INVENTION

The present invention relates to a new use of a known medicament. Specifically, the invention relates to methods and compositions for enhancing the therapeutic efficacy of a therapeutic agent by increasing the uptake of the therapeutic agent by target cells, and in particular relates to a pharmaceutical composition comprising a regulating agent of lipid raft/caveolae-dependent endocytic pathway and some therapeutic agents, such as anti-tumor agents. The invention also relates to a method for screening a regulating agent of lipid raft/caveolae-dependent endocytic pathway capable of enhancing the therapeutic efficacy of anti-tumor agents.

BACKGROUND OF INVENTION

Tumor growth and migration are dependent on angiogenesis and lymphangiogenesis. Therefore, tumor angiogenic and lymphangiogenic endothelial cells have emerged as new targets for cancer therapeutics (Folkman, J. N Engl J Med 1971; 285:1182-1186, Witte M H et al. Lymphology. 1987; 20(4):257-66). Meanwhile, it has been shown that abnormal angiogenesis is also involved in a variety of diseases including obesity, diabetic retinopathy, persistent hyperplastic vitreous, psoriasis, allergic dermatitis, arthritis, arteriosclerosis, endometriosis, asthma, ascites, and peritoneal adhesion (Carmeliet P., Nature Medicine 2003; 9(6): 653-660).

Endostatin (ES) is a 20 kDa C-terminal fragment of collagen XVIII and is an endogenous inhibitor of angiogenesis and lymphangiogenesis. ES can inhibit the proliferation and migration of angiogenic and lymphangiogenic endothelial cells, and thus can impede the formation of new blood vessels and lymphatic vessels. It has been shown that recombinant endostatin can inhibit the growth and metastasis of various types of tumors without eliciting drug resistance in animal models (Folkman J. et al. Cell 1997; 88:277-285, Folkman J. et al. Nature 1997; 390:404-407, Zhuo W. et al, Journal of Pathology; 222:249-260). Recently, a recombinant human endostatin, Endu, containing an extra N-terminal (M)GGSHHHHH amino acid residues compared to the natural endostatin, has been widely used and tested in clinic for the treatment of multiple types of cancers, especially non-small cell lung cancer. It has been shown that ES can be internalized by activated angiogenic and lymphangiogenic endothelial cells. However, the specific mechanism remains unclear.

Epithelial Growth Factor Receptor (EGFR) is overexpressed on the surface of various types of tumor cells and is closely related to the proliferation and metastasis of tumor cells. Several monoclonal antibodies against EGFR have been developed as antitumor therapeutics. For example, Cetuximab is a monoclonal antibody of EGFR that specifically binds to cell surface EGFR of tumor cells. Cetuximab has been used for the treatment of certain cancers.

Nystatin (NT) is a polyene antibiotic that is used as a broad spectrum antifungal drug in human. It can be orally or topically applied, without any interaction with other drugs. NT has high efficacy against *Candida*, while other fungi including *cryptococcus neoformans*, *aspergillus*, *mucor*, *microsporum*, *histoplasma capsulatum*, *blastomyces dermatitidis*, *dermatophytes* are usually sensitive to NT as well. NT is also commonly used as a prophylactic treatment in patients prone to fungal infection, such as AIDS patients and patients undergoing chemotherapy. The mechanism of nystatin and its analogs (e.g., amphotericin B) is that they can bind with ergosterol on the fungus cell membrane, resulting in membrane perforation, potassium leakage, and subsequently the death of fungus. Since ergosterol is a unique lipid composition of fungus cell membrane, NT and amphotericin B will not affect eukaryotic cell membrane when applied to human or animals.

NT can influence the cholesterol-dependent endocytosis of cells and has been used as a specific inhibitor of lipid raft/caveolae-dependent endocytic pathway. Since cholesterol is required for lipid raft/caveolae-dependent endocytic pathway, NT can bind with cell surface membrane cholesterol, thus inhibiting this pathway. Amphotericin B, methyl-β-cyclodextrin, and filipin have a similar function to that of NT and can also inhibit lipid raft/caveolae-dependent endocytic pathway by affecting cholesterol. Amphotericin B (AMB) has the same function as NT and is used for the treatment of *cryptococcus* and *aspergillus* infection.

Wickstrom et al (2002, 2003) reported that in endothelial cells, ES can bind to integrin alpha5beta1 and caveolin (the structural protein of caveolae) in lipid rafts, indicating the correlation between ES and lipid raft (Wickstrom et al, Cancer Res. 2002; 62: 5580-9, Wickstrom et al, J. Biol. Chem. 2003; 278(39): 37895-37901). In addition, Dixelius et al (2000), Shi et al (2007), and Zhuo et al (2010) respectively reported that ES can be specifically internalized in angiogenic and lymphangiogenic endothelial cells (Dixelius et al, Blood 2000, 95, 3403-3411; Shi et al, Blood 2007, 110, 2899-2906, Zhuo W. et al, Journal of Pathology; 222:249-260).

In 2002, Pike et al and Roepstorff et al found that the cell surface binding of epithelial growth factor (EGF), the ligand of EGFR, can be increased by inhibition of cholesterol and lipid rafts (Pike et al, Biochemistry 2002; 41: 10315-22, Roepstorff et al, J Biol Chem 2002; 277: 18954-60).

Kojic et al (2008) reported that tumor cells can internalize AMF/PGI through the lipid raft/caveolae-dependent endocytic pathway. In addition, this endocytic process is cell-type specific, indicating that lipid raft/caveolae-dependent endocytosis might provide a drug delivery route specifically targeting tumor cells (Kojic et al, PLoS ONE 2008; 3: e3597). Migalovich et al (2009) reported that NT increases the uptake of daidzein-BSA by ovarian cancer cells through regulating lipid raft/caveolae-dependent endocytosis. Daidzein-BSA is a potential tumor imaging agent. By increasing the uptake of daidzein-BSA by tumor cells, NT may improve the effects of this tumor imaging agent in tumor imaging (Migalovich et al, Cancer Res. 2009; 69: 5610-5617). In conclusion, lipid raft/caveolae-dependent endocytosis may be involved in the uptake of many important molecules including cytokines, exogenous proteins, and even therapeutic compounds. Regulating and manipulating such endocytic procedures at a cellular level may influence the uptake of these substances in a subject, which may find a potential application for drug delivery.

SUMMARY OF INVENTION

The invention is based on the following discovery. ES can be internalized by endothelial cells through both lipid raft/caveolae-dependent endocytic pathway and clathrin-coated pit endocytic pathway. The inventors surprisingly found that inhibiting lipid raft/caveolae-dependent endocytic pathway with NT leads to an unexpected result that the uptake of ES by angiogenic and lymphangiogenic endothelial cells is increased, resulting in an enhanced inhibitory effect of ES on endothelial cells, tumor angiogenesis, and tumor growth. Without being bound by theory, it is speculated that the inhibition of lipid raft/caveolae-dependent endocytic pathway leads to the compensatory activation of the highly efficient clathrin-coated pit endocytic pathway, resulting in an increased overall endocytosis of ES.

Similarly, ligands of EGFR have been shown to have a similar endocytic machinery to ES. For example, monoclonal antibody against EGFR is a potent antitumor agent that inhibits the signal activation and tumor proliferation by specifically binding to EGFR on tumor cell surface. The inventors found that, by affecting lipid raft/caveolae-dependent endocytosis, NT significantly enhances the uptake of EGFR monoclonal antibody by tumor cells, leading to enhanced therapeutic efficacy of this antibody. These findings indicate the potential use of NT in tumor therapy and imaging. Furthermore, there are many protein drugs sharing a similar endocytic pattern like ES, including endothelin receptor type A, cholera toxin, transforming growth factor-β receptors, B cell antigen receptor, bone morphogenetic protein receptor, HM 1.24, and integrins. These proteins all have the potential to be used in combination with NT to achieve an enhanced therapeutic effect.

Accordingly, in one aspect, the invention provides the use of a regulating agent of lipid raft/caveolae-dependent endocytic pathway in preparing a pharmaceutical composition for increasing the uptake of a therapeutic agent by a target cell in a subject.

In another aspect, the invention provides a method of increasing the uptake of a therapeutic agent by a target cell in a subject, comprising the step of administering a regulating agent of lipid raft/caveolae-dependent endocytic pathway to the subject.

In another aspect, the invention provides a regulating agent of lipid raft/caveolae-dependent endocytic pathway for use in increasing the uptake of a therapeutic agent by a target cell in a subject.

In another aspect, the invention provides a pharmaceutical composition comprising a regulating agent of lipid raft/caveolae-dependent endocytic pathway and a therapeutic agent, such as an antitumor agent.

In specific embodiments of the aforementioned aspects of this invention, the regulating agent of lipid raft/caveolae-dependent endocytic pathway is an inhibitor of lipid raft/caveolae-dependent endocytic pathway. Examples of such inhibitors are polyene antifungal drugs (for example, NT or AMB), methyl-β-cyclodextrin, or filipin.

According to this invention, the aforementioned therapeutic agent is one which can be internalized by a target cell through both lipid raft/caveolae-dependent endocytic pathway and clathrin-coated pit endocytic pathway.

According to this invention, the subject has an angiogenesis-related disease or a lymphangiogenesis-related disease.

According to this invention, the subject suffers from a cancer, for example, lung cancer, pancreatic cancer, liver cancer, stomach cancer, colorectal cancer, esophageal cancer, nasopharyngeal cancer, melanoma, osteocarcinoma, lymphoma, breast cancer, cervical cancer, prostate cancer, hemangioma, neuroendocrine tumor, oral cancer, sarcoma, renal cancer, or biliary duct cancer.

According to this invention, the aforementioned therapeutic agent is an angiogenic or lymphangiogenic inhibitor such as ES and its derivatives. The ES can be a native endostatin or a recombinant endostatin (such as recombinant human endostatin). In a specific embodiment of this invention, the ES has the amino acid sequence of SEQ ID NO.1, SEQ ID NO.2, SEQ ID NO.3, or SEQ ID NO.4. In a further embodiment of this invention, the ES derivatives are PEG-modified endostatin. Preferably, the PEG is monomethoxy PEG with an average molecular weight of 5-40 kDa. An example of the PEG reagent is monomethoxy PEG propionaldehyde. According to a specific embodiment of this invention, the monomethoxy PEG propionaldehyde has an average molecular weight of 20 kDa and the modification site is the N-terminal α-amino group of ES.

According to this invention, the therapeutic agent is an antibody capable of inhibiting the growth of tumors. In a specific embodiment of this invention, the antibody is EGFR antibody, such as a monoclonal antibody against EGFR. An example of the monoclonal antibodies against EGFR is Cetuximab.

In specific embodiments of the aforementioned aspects of this invention, the regulating agent of lipid raft/caveolae-dependent endocytic pathway can be administered by a parenteral route selected from a group of intravenous injection, intravenous infusion, subcutaneous injection, muscle injection, intraperitoneal injection, subcutaneous implant, percutaneous absorption, and hepatic artery injection. Preferably, the regulating agent of lipid raft/caveolae-dependent endocytic pathway is formulated as a liposome-embedded form.

This invention also provides a pharmaceutical composition comprising the aforementioned therapeutic such as ES or antibody and the regulating agent of lipid raft/caveolae-dependent endocytic pathway.

In another aspect, this invention also provides a method of screening for a functional regulating agent of lipid raft/caveolae-dependent endocytic pathway that may have an enhancement effect on antitumor therapeutics.

This invention also relates to a combined therapy, a combined formulation, or a pharmaceutical composition comprising a drug or agent that has a similar mechanism to that of NT (such as AMB), and a therapeutic agent that has a similar endocytic and acting mechanism to that of ES or EGFR antibody.

BRIEF DESCRIPTION OF THE DRAWINGS

FIGS. 1A-E: NT and its analogs (AMB, methyl-β-cyclodextrin, and filipin) enhance the internalization of ES and its derivatives (or modified derivatives) in endothelial cells in a dose-dependent manner.

A: Western Blotting analysis showing that NT enhanced the internalization of ES in endothelial cells in a dose-dependent manner and the enhancement was positive correlated with the concentrations of NT. This enhancement is evidenced by the increased accumulation of ES in cytosolic fraction, nuclear fraction, and whole cell lysate, compared with the condition without NT treatment.

B: Western Blotting analysis showing that NT dose-dependently enhanced the internalization of ES in lymphatic endothelial cells.

C: Western Blotting analysis showing that AMB, methyl-β-cyclodextrin, and filipin dose-dependently enhanced the internalization of ES in endothelial cells.

D: Western Blotting analysis showing that NT dose-dependently enhanced the internalization of PEG-modified ES in endothelial cells.

E: Western Blotting analysis showing that NT enhanced the internalization of Endu [recombinant human endostatin containing an additional (M)GGSHHHHH amino acid sequence (SEQ ID NO:5) at N-terminal] and N-terminal-PEG-single-point-modified Endu (PEG-Endu) in endothelial cells in a dose-dependent manner and the enhancement was positive correlated with NT concentration.

FIGS. 3A-B: Combination treatment with NT and ES enhances the inhibitory effect of ES on the migration of endothelial cells.

A: Cell migration assay confirmed that combination treatment with NT and ES enhanced the inhibitory effect of ES on the activity of endothelial cells, as evidenced by a decrease in the number of migrated cells compared with ES treatment without NT.

B: Statistic data of the migrated cell number in cell migration assay, representing the migration ability of endothelial cells in each treatment group.

FIGS. 4A-E: Combination therapy with NT and ES enhances the inhibitory effects of ES on tumor growth and improve the distribution of ES in tumor tissue.

A: Combination therapy with NT and ES enhanced the inhibitory effect of ES on tumor growth in A549 non-small cell lung cancer animal model.

B: Immunofluorescence assay confirmed that combination therapy with NT and ES enhanced the inhibitory effect of ES on tumor angiogenesis in A549 animal model.

C: Combination therapy with NT and ES enhanced the inhibitory effect of ES on tumor growth in H22 liver cancer animal model.

D: Immunofluorescence assay confirmed that combination therapy with NT and ES enhanced the inhibitory effect of ES on tumor angiogenesis in H22 liver cancer animal model.

E: Fluorescence imaging assay confirmed that combination therapy with NT and ES enhanced the uptake and distribution of ES (containing rhodamine fluorescent label) within tumor tissue in tumor-bearing animal model.

FIGS. 5A-B: NT enhances the uptake of EGFR monoclonal antibody in tumors.

A: Western Blotting analysis showing that NT enhanced the internalization of EGFR monoclonal antibody in tumor cells in a dose-dependent manner.

B: In vivo fluorescence imaging assay confirmed that combination therapy with NT and EGFR monoclonal antibody enhanced the uptake and distribution of EGFR monoclonal antibody within tumor tissues in a tumor-bearing animal model.

DETAILED DESCRIPTION

The present invention provides a new use for a broad-spectrum polyene antibiotic Nystatin (NT) and similar agents. In addition, the present invention provides new pharmaceutical compositions and methods of applying the same for enhancing the efficacy of therapeutic protein drugs, such as ES and EGFR monoclonal antibody, which are internalized by means of lipid raft/caveolae-dependent endocytic pathway and clathrin-coated pit endocytic pathway.

Lipid rafts are the micro-domains on plasma membrane rich in cholesterol and sphingomyelins. The saturated aliphatic chains of sphingomyelins and glycosphingolipids are clustered tightly and the gaps between the saturated aliphatic chains are filled with cholesterol as spacer molecules to form a liquid-ordered phase, i.e. lipid raft, which is about 50 nm in diameter. Lipid raft is a dynamic structure that has a close relationship with the cell membrane signal transduction and protein sorting.

Caveolae (also known as membrane cave-like invagination or membrane microcapsules) refers to a form of lipid raft which has the same membrane lipids composition as lipid raft, but also contains caveolin (a small-molecular-weight protein, 21 kDa). Lipid raft/caveolae-dependent pathway does not require clathrin. Adipocytes, endothelial cells, epithelial cells and smooth muscle cells are abundant in caveolae which is involved in endocytosis. In addition, the presence of certain signal molecules in caveolae indicates that it is associated with cell signal transduction.

Clathrin-coated pits are dynamic membrane transporting structure formed during the process of the clathrin-mediated endocytosis. Endocytosis that are dependent on this type of structure is called the clathrin-mediated endocytosis.

Angiogenesis-related diseases and lymphangiogenesis-related diseases are diseases closely related to abnormal angiogenesis and lymphangiogenesis, including cancer, autoimmune diseases like arthritis and psoriasis, diabetes, obesity and a variety of eye diseases.

The inventors found that lipid raft/caveolae-dependent endocytic pathway inhibitor NT can significantly enhance the endocytosis of ES in vascular endothelial cells when both NT and endostatin are added to the culture media of vascular endothelial cells. This enhancement effect is positively correlated with the concentrations of NT. Meanwhile, the same result was also observed in lymphatic endothelial cells.

Further experiments revealed that this enhancement effect can also be achieved by other therapeutic agents and reagents with the similar action mechanism to NT. As demonstrated in Example 1, a class of substances with the similar action mechanism to NT, such as amphotericin B (AMB), methylated β-cyclodextrin (Ma-CD) and filipin, can also enhance the endocytosis of ES in vascular endothelial cells. AMB and filipin are antifungal antibiotics. Similar to NT, AMB, M-CD and filipin can significantly enhance the endocytosis of ES in vascular endothelial cells, and this enhancement effect is positively correlated with the concentrations of these compounds.

Moreover, the inventors found that NT can significantly enhance the endocytosis of PEG-modified ES (PEG-ES), ES with additional amino acid sequence (M)GGSHHHHH (SEQ ID NO:5) at N-terminal (Endu), and Endu with PEG modification at N-terminal in endothelial cells, and this enhancement effect is positively correlated with the concentrations of NT.

At the molecular cell biology level, the inventors demonstrated that NT can promote the endocytosis of ES in endothelial cells, and further enhance the inhibitory effect of ES on endothelial cell survival related signaling pathways (such as ERK and p38 MAPK).

At the cellular level, the inventors demonstrated that the combination of NT and ES can enhance the inhibitory effect of ES on endothelial cell migration activity. Further, using the A549 lung cancer animal model and the H22 liver cancer animal model, the inventors demonstrated that NT can enhance the inhibitory effect of ES on tumor growth and tumor angiogenesis. In addition, it is found that NT can also enhance the uptake and distribution of ES in tumor tissues.

The inventors also found that, EGFR monoclonal antibody has some similarities to ES in terms of its endocytic mechanism, and its endocytosis in tumor cells can also be modulated by NT. At the molecular cell biology level, the inventors demonstrated that NT can enhance the endocytosis of EGFR monoclonal antibody in cancer cells. Further, the inventors also demonstrated that combined treatment with NT and EGFR monoclonal antibody can improve the distribution and uptake of EGFR monoclonal antibody in xenograft tumor in mice.

Accordingly, the invention provides a new use of antifungal antibiotic NT in a combined anticancer therapy to promote the uptake and efficacy of anticancer agents such as ES or EGFR monoclonal antibody. It may be used in cancer treatment and tumor imaging.

Protein modification with polymers is a commonly used technique to change the dynamic characteristics of drugs, such as half-life, and to improve immunological characteristics and toxicological properties. Among the polymers, the polyethylene glycol (PEG) is the most commonly used protein modification molecule. The inventors proved that the endocytosis of endostatin (and its derivative Endu) modified with PEG (monomethoxy polyethylene glycol propionaldehyde) at the N-terminal α-amine was significantly increased in endothelial cells by NT. This fact provides a theoretical basis for the combination therapy of NT and modified or labeled ES or its derivatives to achieve a synergistic effect.

The inventors also demonstrated that this combined therapy can be extended to other drugs which have similar endocytic pattern and action mechanism to ES. Such drugs include substances which can target tumor or tumor vasculature and thus can be used for treatment or imaging purposes, such as EGFR monoclonal antibody and the modified, labeled EGFR monoclonal antibody. The uptake and efficacy of such substances can also be promoted when used in combination with polyene agents such as NT.

The invention also provides a new formulation and pharmaceutical composition for the combined therapy of NT (or AMB, etc.) and ES. ES is administered by intravenous infusion in cancer therapy. NT is a broad-spectrum antifungal polyene antibiotic, insoluble in water and difficult to be absorbed in gastrointestinal tract after oral administration, having high toxicity by direct injection. However, it has been shown that NT can be administered as an intravenous infusion by way of liposome encapsulation. For example, Aronex's NT liposomal formulation, Nyotran, completed phase III clinical trials in 1999 and is expected to be commercialized in recent years. This will allow intravenous administration of NT. Both AMB and NT belong to broad-spectrum antifungal polyene antibiotics, and they share the identical action mechanisms. To date, there are three kinds of amphotericin B liposome formulations listed in European and American market (trade name: Abelcet, Amphocil and AmBisome, respectively), which achieve intravenous infusion for this kind of insoluble antibiotics. Another liposomal amphotericin B infusion formulation was also released in 2003, under the trade name Fungizone. Therefore, it is feasible to achieve the combination therapy of ES or EGFR monoclonal antibody with NT or AMB by way of liposome formulations and intravenous administration.

EXAMPLES

Example 1

NT Enhances the Uptake and Internalization of ES in Blood Vessel Endothelial Cells and Lymphatic Vessel Endothelial Cells Human microvascular endothelial cells (HMECs) were from ATCC (accession number CRL 10636). Mouse lymphatic endothelial cells (mLEC) were isolated via digesting peritoneal lymphoma induced by incomplete Freund's adjuvant injection (Zhuo W. et al, Journal of Pathology; 222:249-260). Endu was obtained from Simcere-Medgenn Bio-pharmaceutical Co., Ltd. Endu is a recombinant ES containing an additional amino acid sequence (M)GGSHHHHH (SEQ ID NO:5) at N-terminal, the sequence of which is SEQ ID NO.3 or SEQ ID NO.4 because the first amino acid residue M will be randomly deleted when expressed in $E.\ Coli$. ES was obtained from Protgen Ltd., the amino acid sequence of which is SEQ ID NO.1 or SEQ ID NO.2 because the first amino acid residue M will be randomly deleted when expressed in $E.\ Coli$. Monomethoxy PEG propionaldehyde (mPEG-ALD) with an average molecular weight of 20 kDa (Jenkem Technology CO., Ltd.,) was used as the PEG reagent for specifically modifying the α-amino group at N-terminal of a protein. PEG-ES and PEG-Endu were prepared by Protgen Ltd. according to the instructions provided in the PEG reagent kit. Monoclonal antibody against ES was purchased from Oncogene Science, Inc. NT and other reagents were purchased from Sigma-Aldrich Co.

Figure 1:
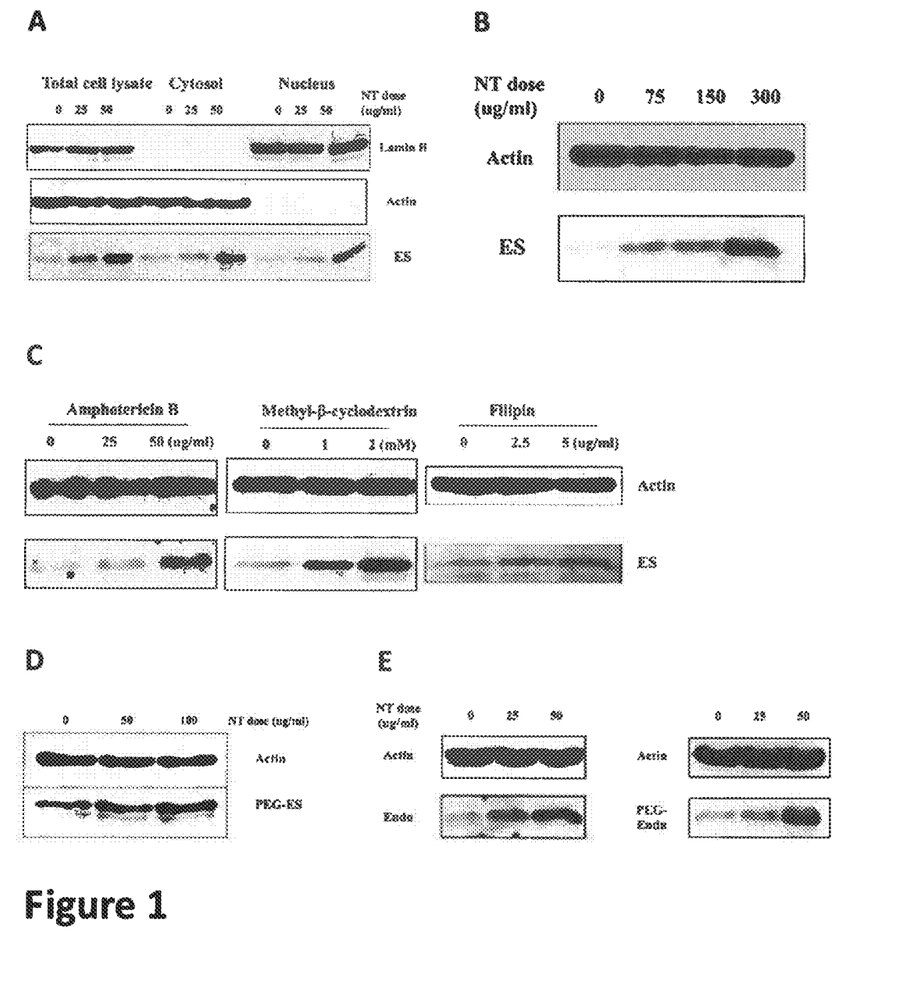

The endothelial cells were cultured to reach 90% confluence, and then pre-treated with DMEM medium (Hyclone) containing NT as follows. NT stock solution was added to the medium to a final concentration of 0 μg/mL, 25 μg/mL, or 50 μg/mL, and the culture was then incubated in a 5% $CO_2$ atmosphere at 37° C. for 20 min for NT pre-treatment. After pre-treatment, ES stock solution (5 mg/ml) was added to the medium to a final concentration of 5 μg/mL. The culture was then incubated in a 5% $CO_2$ atmosphere at 37° C. for 30 min to allow the internalization of ES by the endothelial cells. After removing the medium, the endothelial cells were washed with ice-cold PBS for 3 times and then collected. The ES internalization in whole cell lysate, cytosolic fraction, and nuclear fraction was examined by Western Blotting, compared with the cells without NT treatment. The results indicated that under the same ES dosage and treatment time, NT treatment significantly increased the ES internalization in whole cell lysate, cytosolic fraction, and nuclear fraction (FIG. 1A). The ES internalization was increased by about 2 folds and 15 folds in cells treated with NT at 25 μg/mL and 50 μg/mL, respectively, and the increase of ES internalization was positively correlated to NT concentration (FIG. 1A).

The mLECs were pre-treated with DMEM (Hyclone) containing 0, 75, 150, or 300 μg/mL NT in a 5% $CO_2$ atmosphere at 37° C. for 20 min. The cells were then incubated with culture media containing ES (final concentration of 2 μg/mL) in a 5% $CO_2$ atmosphere at 37° C. for 15 min. After treatment, the cells were washed with PBS for 3 times, and then collected. The ES internalization in cells treated with NT at various concentrations was examined by Western Blotting. The results showed that treatment with NT at 75, 150, 300 μg/mL increased ES internalization in mLECs by 16-, 32- and 78-fold, respectively, and the increase of ES internalization was positively correlated to NT concentration (FIG. 1B).

Some other agents which share the same action mechanism as NT were also tested in place of in this example, such as AMB (25-50 µg/mL), methyl-β-cyclodextrin (1-2 mM), and filipin (2.5-5 µg/mL). The results showed that they can increase ES internalization in endothelial cells (FIG. 1C).

Other therapeutic agents which share the same action mechanism as ES can also be used in this example, such as PEG-modified ES. For this purpose, ES was modified with monomethoxy PEG propionaldehyde (mPEG-ALD) of 20 kDa which specifically modifies the N-terminal of a protein, and the product (PEG-ES) was an ES protein conjugated with one PEG molecule at the N-terminal α-amino group of ES. The results indicated that under the same PEG-ES dosage and treatment time, PEG-ES internalization in blood vessel endothelial cells was increased with NT treatment, and the increases were positively correlated to the NT concentrations (FIG. 1D).

Similar results were also obtained in internalization experiment using other derivatives of ES, Endu and PEG-Endu (Endu conjugated with one PEG group on the N-terminal α-amino group). Under the same dosage and treatment time, Endu/PEG-Endu internalization in endothelial cells was increased with NT treatment, and the increases were positively correlated to the NT concentration (FIG. 1E).

Example 2

NT Increases the Inhibitory Effect of ES on Endothelial Cell Signal Pathways by Enhancing ES Internalization Kim et al (2002) found that ES can inhibit the signal transduction pathways in endothelial cell mediated by extracellular regulated protein kinases (ERK), p38 mitogen-activated protein kinases (MAPK), and p125 focal adhesion kinase (p125 FAK), resulting in the inhibition of endothelial cell activity (Kim et al, J. Biol. Chem. 2002, 277, 27872-27879). In this example, the ERK and p38 MAPK pathways were taken as the markers of endothelial cell activation and it is found that the combination of NT and ES further elevated the inhibitory effect of ES on these pathways.

Figure 2:
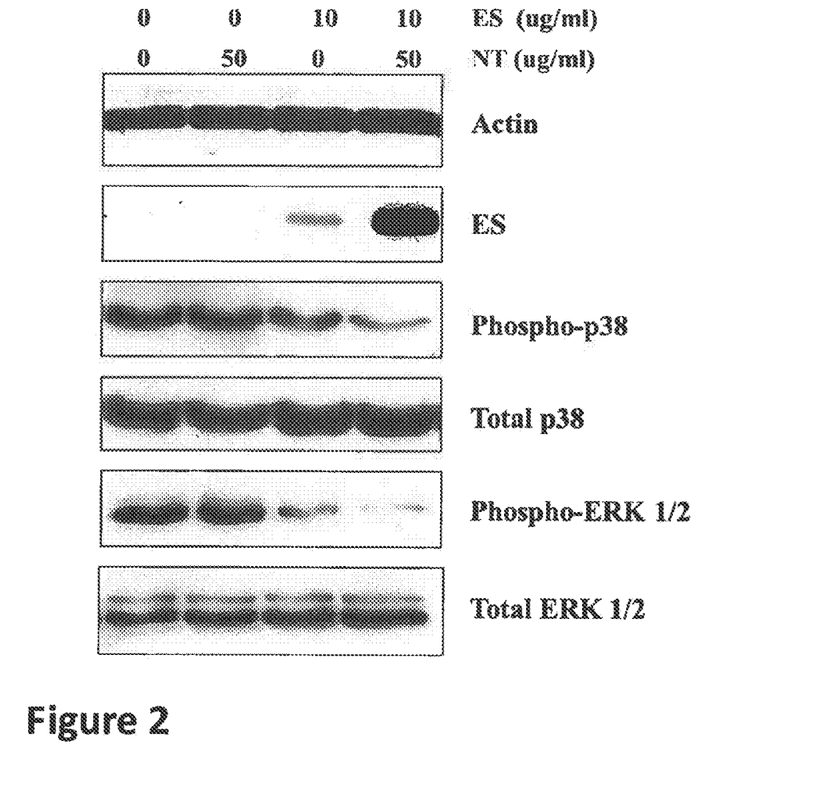
FIG. 2: Western Blotting analysis showing that combination treatment with NT and ES enhanced the internalization of ES by endothelial cells and enhanced the inhibitory effect of ES on ERK and p38 MAPK signaling pathways in endothelial cells.

In this example, endothelial cells were separated into four groups: (1) negative control group, neither NT treatment, nor ES treatment; (2) NT group, treatment with NT at 50 µg/mL for 20 min, without ES treatment; (3) ES group, treatment with ES at 5 µg/mL for 30 min, without NT treatment; (4) NT plus ES group, treatment with NT at 50 µg/mL for 20 min, followed by treatment with ES at 5 µg/mL for 30 min. After treatment with the same method as described in Example 1, cells were collected and the ERK and p38 MAPK pathways were examined. The results showed that compared with negative control group, NT treatment (NT group) did not influence the signal transduction of ERK and p38 MAPK pathways. ES treatment (ES group) inhibited the activation of ERK and p38 MAPK pathways, which is consistent with that reported by Kim et al. NT plus ES treatment (NT plus ES group) further enhanced the inhibitory effects of ES on the activation of ERK and p38 MAPK pathways. These results demonstrated that combined treatment with NT plus ES potentiated the inhibitory effect of ES on the activation of cell signaling pathways (FIG. 2).

Example 3

NT Enhances the Inhibitory Effect of ES on Endothelial Cell Migration

Cell migration assay: HMEC ($2\times10^4$ cells per well) were seeded into DMEM (Hyclone) containing 0.5% FBS (Hyclone) and 10 ng/mL VEGF (PeproTech) on the upper layer of Transwell chambers (8 µm pores, Costar). ES (40 µg/mL) or NT (50 µg/mL) was added into both the upper and lower layers, and then the chambers were incubated in a 5% $CO_2$ atmosphere at 37° C. for 6 hours to allow cell migration. After glutaraldehyde fixation and crystal violet staining, 5 randomly selected fields in each well were observed with a microscopy (400× magnification, Olympus IX71). The numbers of the cells migrated into the lower layer were counted and mean values were calculated. Experiments were performed in triplicate and each experiment was repeated twice.

Figure 3:
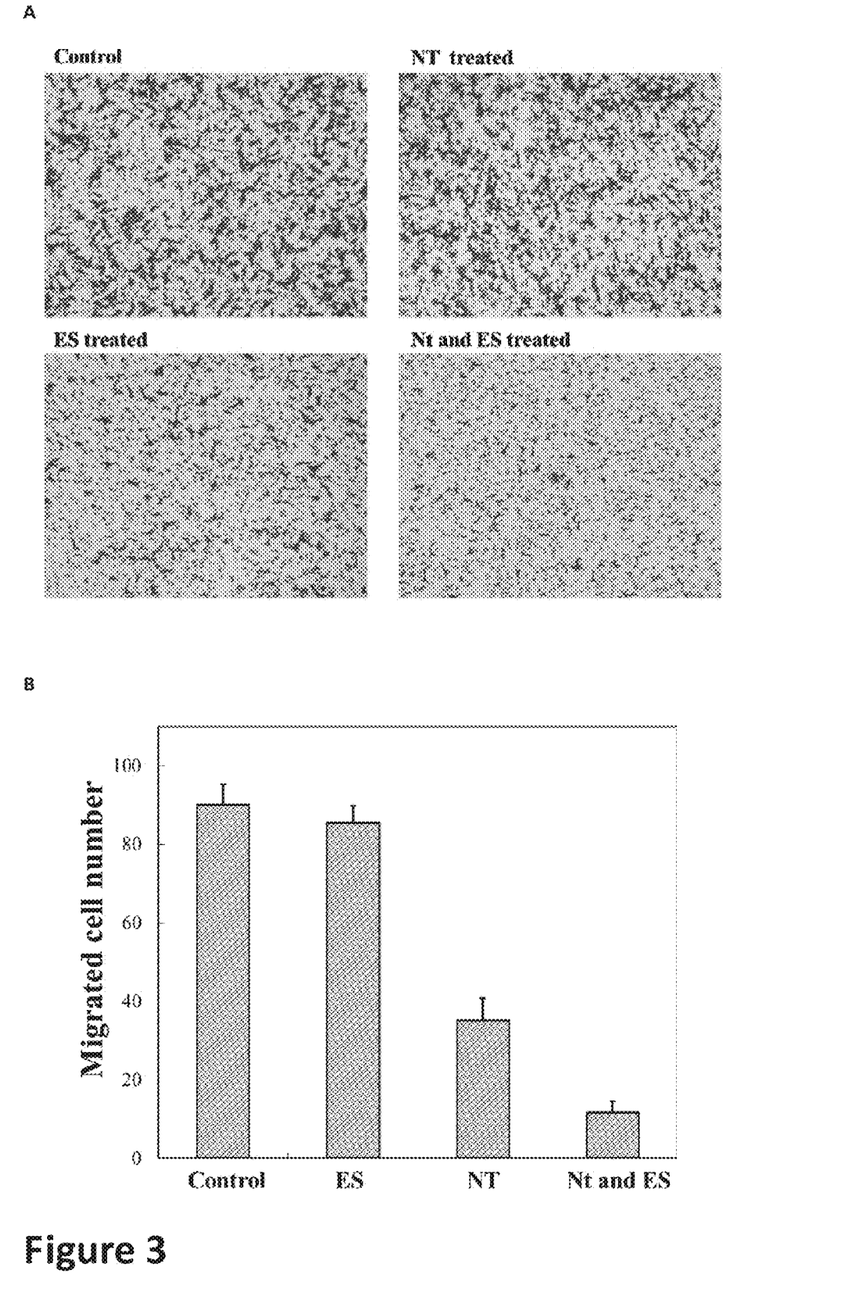

In this example, endothelial cells were separated into four groups: (1) negative control group, neither NT treatment, nor ES treatment; (2) NT group, treatment with NT at 50 µg/mL, without ES treatment; (3) ES group, treatment with ES at 40 µg/mL, without NT treatment; (4) NT plus ES group, combined treatment with NT at 50 µg/mL and ES at 40 µg/mL. The results showed that compared with negative control group, NT treatment (NT group) did not substantially influence the transwell migration of endothelial cells. ES treatment (ES group) inhibited the transwell migration of endothelial cells by 61%. NT plus ES treatment (NT plus ES group) enhanced the inhibitory effect of ES on the transwell migration of endothelial cells (inhibition rate 87%, P<0.001, NT plus ES group vs ES group). These results demonstrated that combined treatment with NT plus ES potentiated the inhibitory effect of ES on endothelial cell migration. Representative images of cell migration in each group were shown in FIG. 3A. Mean values of migrated cell numbers were shown in FIG. 3B.

Example 4

Figure 4:
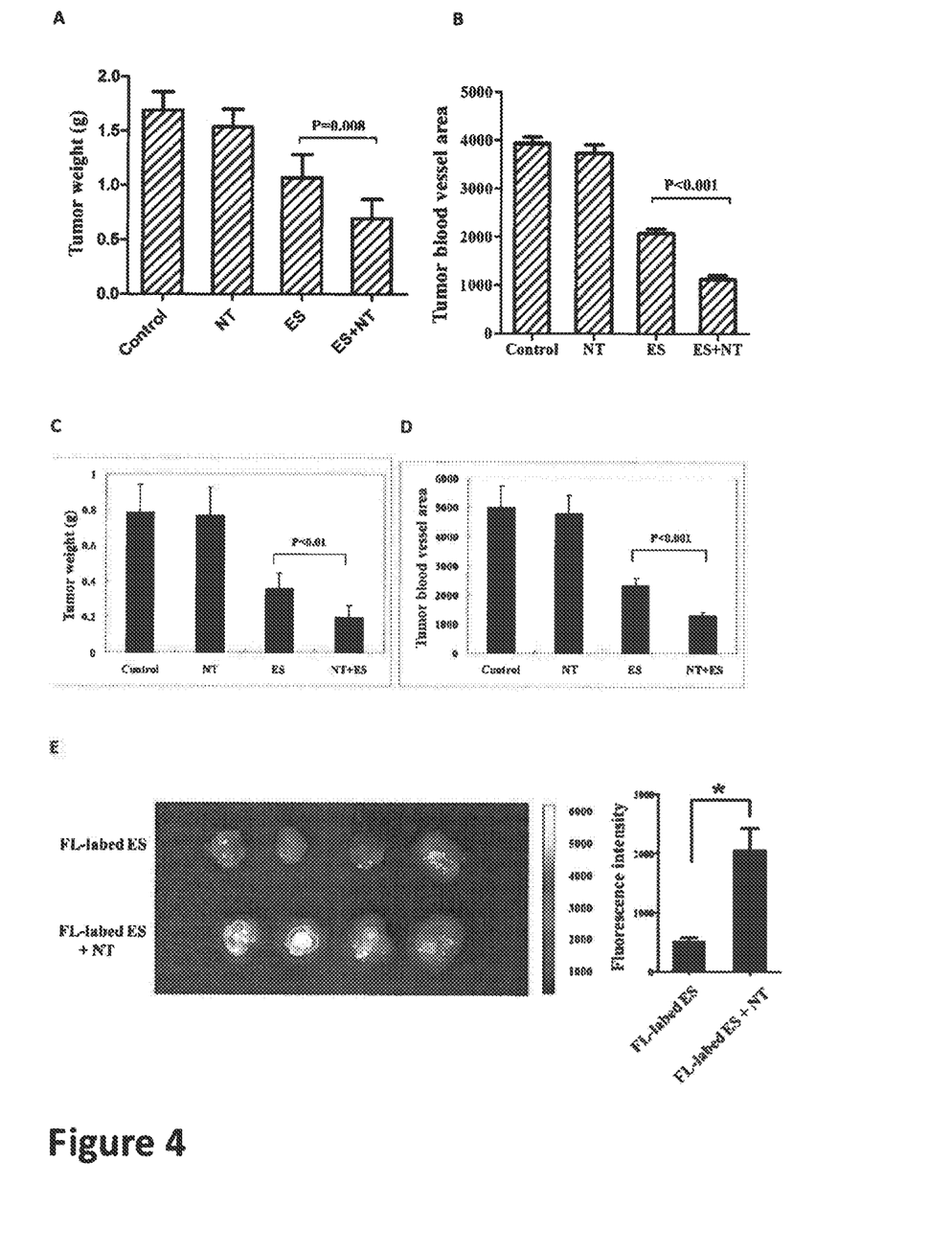

NT Increases the Uptake and Distribution of ES in Tumor Tissue, Resulting in Enhanced Antitumor and Antiangiogenesis Efficacy of ES in Animals Human lung adenocarcinoma A549 tumor cells (ATCC accession number CCL-185) at exponential growth were subcutaneously inoculated into 6-8 week-old nude mice (Vital River Laboratory Animal Technology Co., Ltd). When the tumor volume reached 100 $mm^3$, the tumor bearing nude mice were separated into four groups: (1) negative control, treatment with saline; (2) NT group, treatment with NT (6 mg/kg, intraperitoneal injection, daily), without ES treatment; (3) ES group, treatment with ES (12 mg/kg, intraperitoneal injection, daily), without NT treatment; (4) NT plus ES group, combined treatment with NT (6 mg/kg, intraperitoneal injection, daily) and ES (12 mg/kg, intraperitoneal injection, daily). After fourteen daily injections, mice were sacrificed, and the weight and volume of the tumors were measured. The results indicated that compared with control group, NT treatment did not influence tumor growth; ES treatment inhibited tumor growth by 40%. NT plus ES treatment enhanced the inhibitory effect of ES on tumor growth (inhibition rate 60%). These results demonstrated that NT potentiated the inhibitory efficacy of ES on tumor growth (FIG. 4A). No abnormal changes were observed in the animals in all groups in terms of weight, feeding and routine.

Tumor blood vessel formation assay: Tumors from A549 mice were resected, fixed and sectioned. Samples were detected with primary antibody against CD31 (the marker of tumor blood vessel endothelial cells) and FITC-labeled secondary antibody (Santa Cruz), and then observed with Nikon A1 laser scanning confocal microscope (LSCM). The sectional areas of blood vessels in randomly selected fields (400×) were quantified and averaged with the software of the LSCM system. The results showed that NT potentiated the inhibitory efficacy of ES on tumor blood vessel formation, which was similar to the inhibitory efficacy on tumor growth. Average tumor weight of each group was shown in FIG. 4A. Average tumor blood vessel area (arbitrary unit) of each group was shown in FIG. 4B.

The enhancement effect of NT on the antitumor and anti-angiogenesis activities of ES was also evidenced in H22 liver cancer mouse model. Average tumor weight in each group was shown in FIG. 4C. Average tumor blood vessel area (arbitrary unit) in each group was shown in FIG. 4D. No abnormal changes were observed in the animals in all groups in terms of weight, feeding and routine.

Measurement of the uptake and distribution of fluorescent-labeled ES in tumor tissue of tumor-bearing mice: Human lung adenocarcinoma A549 tumor cells at exponential growth were subcutaneously inoculated into 6-8 week-old nude mice (Vital River Laboratory Animal Technology Co., Ltd). Tumor-bearing mice (n=4/group) were separated into two groups when the tumor volume reached 300 mm$^3$. (1): ES group, treatment with Rhodamine (Pierce) labeled ES (Rh-ES, 20 mg/kg, intraperitoneal injection), without NT; (2) NT plus ES group, combined treatment with NT (6 mg/kg, intraperitoneal injection) and Rh-ES (20 mg/kg, intraperitoneal injection). Four hours later, mice were sacrificed, and the tumors were resected, the imaging and quantitive analysis of fluorescent-labeled-ES uptake in tumor was performed with bioluminescence imaging system (Tsinghua University). The results showed that NT significantly increased the uptake and distribution of ES in tumor tissue by 4 folds (FIG. 4E).

Example 5

Figure 5:
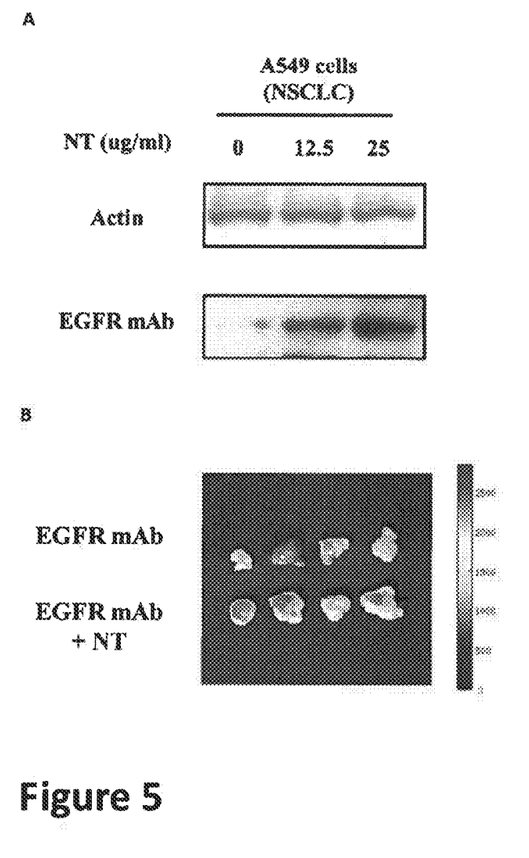

NT Significantly Enhances the Endocytosis of EGFR Monoclonal Antibody (Cetuximab) by Tumor Cells and the Uptake and Distribution of EGFR Monoclonal Antibody in Animal Tumor Tissues EGFR-expressing A549 cells at exponential growth were cultured to reach 90% confluence and then pre-treated with DMEM medium containing NT as follows. NT stock solution was added to the medium to a final concentration of 0 g/mL, 25 μg/mL, or 50 μg/mL, and the culture was then incubated in a 5% $CO_2$ atmosphere at 37° C. for 20 min for NT pre-treatment. After pre-treatment, EGFR monoclonal antibody (Cetuximab, Merck) stock solution (5 mg/ml) was added to the medium to a final concentration of 5 μg/mL. The culture was then incubated in a 5% $CO_2$ atmosphere at 37° C. for 30 min to allow the internalization of EGFR monoclonal antibody by the endothelial cells. After treatment, the medium was removed, and the endothelial cells were washed with ice-cold PBS for 3 times and then collected. The EGFR monoclonal antibody internalization in cells was examined by Western Blotting, compared with EGFR monoclonal antibody internalization in cells without NT treatment. The results showed that under the same Cetuximab dosage and treatment time, NT treatment significantly increased the Cetuximab internalization in the cells, and Cetuximab internalization was positively correlated to NT concentrations (FIG. 5A).

Human lung adenocarcinoma A549 tumor cells at exponential growth were subcutaneously inoculated into 6-8 week-old nude mice (Vital River Laboratory Animal Technology Co., Ltd). The mice (n=4/group) were separated into two groups. When the tumor volume reached about 500 mm$^3$, the first group was treated with Cy5.5-labelled Cetuximab (Cy5.5, GE), and the second group was treated with Cy5.5-labelled Cetuximab (same dose as the first group) plus NT. Cy5.5-Cetuximab uptake in tumors from the two groups of animals was examined with bioluminescence imaging system (Tsinghua University). The results demonstrated that NT can increase the uptake and distribution of Cetuximab in tumor tissues, and thus is useful in enhancing medicine uptake, improving therapeutic efficacy and tumor imaging (FIG. 5B).

The invention claimed is:

1. A method of increasing the uptake of a therapeutic agent by a target cell in a subject comprising administering to a subject in need thereof (i) a therapeutic agent and (ii) an inhibitor of lipid raft/caveolae-dependent endocytic pathway, wherein the therapeutic agent is selected from the group consisting of (i) a naturally occurring endostatin or a derivative thereof, (ii) a recombinant human endostatin or a derivative thereof and (iii) an antibody against epidermal growth factor receptor (EGFR), wherein the inhibitor of the lipid raft/caveolae-dependent endocytic pathway is Nystatin and wherein the subject is suffering from a tumor.

2. The method of claim 1, wherein the endostatin comprises an amino acid sequence as shown in SEQ ID NO.1 or SEQ ID NO.2.

3. The method of claim 1, wherein the endostatin has the amino acid sequence as shown in SEQ ID NO.3 or SEQ ID NO.4.

4. The method of claim 1, wherein the endostatin derivative is a polyethylene glycol (PEG) modified endostatin.

5. The method of claim 4, wherein the polyethylene glycol (PEG) is monomethoxy PEG with an average molecular weight of 5-40 kD.

6. The method of claim 5, wherein the PEG is monomethoxy PEG propionaldehyde.

7. The method of claim 6, wherein the average molecular weight of the monomethoxy PEG propionaldehyde is 20 kD.

8. The method of claim 4, wherein the endostatin is modified by polyethylene glycol (PEG) at the site of its N-terminal α-amine.

9. The method of claim 1, wherein the antibody is a monoclonal antibody against epidermal growth factor receptor (EGFR).

10. The method of claim 9, wherein the monoclonal antibody against epidermal growth factor receptor (EGFR) is Cetuximab.

11. The method of claim 1, wherein the tumor is selected from the group consisting of lung cancer, pancreatic cancer, liver cancer, stomach cancer, colorectal cancer, esophagus cancer, nasopharyngeal carcinoma, malignant melanoma, bone cancer, lymphoma, breast cancer, cervical cancer, prostate cancer, hemangioma, Neuroendocrine tumor, oral cancer, sarcoma, renal cancer and gall bladder cancer.

12. The method of claim 1, wherein the inhibitor of lipid raft/caveolae-dependent endocytic pathway is administered via a parenteral route selected from the group consisting of intravenous injection, intravenous infusion, hypodermic injection, intramuscular injection, intraperitoneal injection, subcutaneous-embed, transdermal absorption, and hepatic arterial injection.

13. The method of claim 12, wherein the inhibitor of lipid raft/caveolae-dependent endocytic pathway is prepared in the form of liposome encapsulation.

14. A pharmaceutical composition comprising: (a) a therapeutic agent which is endostatin or an antibody against epidermal growth factor receptor (EGFR) and (b) an inhibitor of lipid raft/caveolae-dependent endocytic pathway which is Nystatin.

* * * * *

SEQUENCE LISTING

```
<160> NUMBER OF SEQ ID NOS: 5

<210> SEQ ID NO 1
<211> LENGTH: 183
<212> TYPE: PRT
<213> ORGANISM: Homo sapiens

<400> SEQUENCE: 1

His Ser His Arg Asp Phe Gln Pro Val Leu His Leu Val Ala Leu Asn
1               5                   10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125
```

```
Arg Leu Thr Glu Ser Tyr Cys Glu Thr Trp Arg Thr Glu Ala Pro Ser
        130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180

<210> SEQ ID NO 2
<211> LENGTH: 184
<212> TYPE: PRT
<213> ORGANISM: Homo sapiens

<400> SEQUENCE: 2

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Gly Pro Leu Lys
                85                  90                  95

Pro Gly Ala Arg Ile Phe Ser Phe Asp Gly Lys Asp Val Leu Arg His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Ser Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180

<210> SEQ ID NO 3
<211> LENGTH: 192
<212> TYPE: PRT
<213> ORGANISM: Homo sapiens

<400> SEQUENCE: 3

Met Gly Gly Ser His His His His His His Ser His Arg Asp Phe Gln
1               5                   10                  15

Pro Val Leu His Leu Val Ala Leu Asn Ser Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ala Gly Thr Phe Arg Ala Phe Leu Ser Ser Arg Leu Gln
    50                  55                  60

Asp Leu Tyr Ser Ile Val Arg Arg Ala Asp Arg Ala Ala Val Pro Ile
65                  70                  75                  80
```

```
Val Asn Leu Lys Asp Glu Leu Leu Phe Pro Ser Trp Glu Ala Leu Phe
            85                  90                  95

Ser Gly Ser Glu Gly Pro Leu Lys Pro Gly Ala Arg Ile Phe Ser Phe
            100                 105                 110

Asp Gly Lys Asp Val Leu Arg His Pro Thr Trp Pro Gln Lys Ser Val
            115                 120                 125

Trp His Gly Ser Asp Pro Asn Gly Arg Arg Leu Thr Glu Ser Tyr Cys
130                 135                 140

Glu Thr Trp Arg Thr Glu Ala Pro Ser Ala Thr Gly Gln Ala Ser Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Lys
            180                 185                 190
```

<210> SEQ ID NO 4
<211> LENGTH: 191
<212> TYPE: PRT
<213> ORGANISM: Homo sapiens

<400> SEQUENCE: 4

```
Gly Gly Ser His His His His His Ser His Arg Asp Phe Gln Pro
1               5                   10                  15

Val Leu His Leu Val Ala Leu Asn Ser Pro Leu Ser Gly Gly Met Arg
            20                  25                  30

Gly Ile Arg Gly Ala Asp Phe Gln Cys Phe Gln Gln Ala Arg Ala Val
            35                  40                  45

Gly Leu Ala Gly Thr Phe Arg Ala Phe Leu Ser Ser Arg Leu Gln Asp
            50                  55                  60

Leu Tyr Ser Ile Val Arg Arg Ala Asp Arg Ala Ala Val Pro Ile Val
65                  70                  75                  80

Asn Leu Lys Asp Glu Leu Leu Phe Pro Ser Trp Glu Ala Leu Phe Ser
            85                  90                  95

Gly Ser Glu Gly Pro Leu Lys Pro Gly Ala Arg Ile Phe Ser Phe Asp
            100                 105                 110

Gly Lys Asp Val Leu Arg His Pro Thr Trp Pro Gln Lys Ser Val Trp
            115                 120                 125

His Gly Ser Asp Pro Asn Gly Arg Arg Leu Thr Glu Ser Tyr Cys Glu
            130                 135                 140

Thr Trp Arg Thr Glu Ala Pro Ser Ala Thr Gly Gln Ala Ser Ser Leu
145                 150                 155                 160

Leu Gly Gly Arg Leu Leu Gly Gln Ser Ala Ala Ser Cys His His Ala
                165                 170                 175

Tyr Ile Val Leu Cys Ile Glu Asn Ser Phe Met Thr Ala Ser Lys
            180                 185                 190
```

<210> SEQ ID NO 5
<211> LENGTH: 9
<212> TYPE: PRT
<213> ORGANISM: Artificial
<220> FEATURE:
<223> OTHER INFORMATION: His-tag

<400> SEQUENCE: 5

```
Met Gly Gly Ser His His His His His
1               5
```